(12) United States Patent
Curran

(10) Patent No.: US 6,241,679 B1
(45) Date of Patent: Jun. 5, 2001

(54) NON-INVASIVE BLOOD PRESSURE SENSING DEVICE AND METHOD USING TRANSDUCER WITH ASSOCIATE MEMORY

(75) Inventor: Timothy G. Curran, Ramsey, MN (US)

(73) Assignee: Medwave, Inc., Arden Hills, MN (US)

( * ) Notice: Subject to any disclaimer, the term of this patent is extended or adjusted under 35 U.S.C. 154(b) by 0 days.

(21) Appl. No.: 09/317,291

(22) Filed: May 24, 1999

(51) Int. Cl.[7] ............................................. A61B 5/00
(52) U.S. Cl. ................................. 600/485; 600/500
(58) Field of Search ............................ 600/300, 485, 600/500–503, 504, 561, 529

(56) References Cited

U.S. PATENT DOCUMENTS

| | | | |
|---|---|---|---|
| 4,858,615 | * 8/1989 | Meinema | 600/481 |
| 5,241,964 | 9/1993 | McQuilkin | 128/672 |
| 5,269,312 | * 12/1993 | Kawamura et al. | 600/500 |
| 5,425,375 | * 6/1995 | Chin et al. | 600/549 |
| 5,450,852 | 9/1995 | Archibald et al. | 128/672 |
| 5,566,676 | * 10/1996 | Rosenfeldt et al. | 600/485 |
| 5,640,964 | 6/1997 | Archibald et al. | 128/672 |
| 5,642,733 | 7/1997 | Archibald et al. | 128/672 |
| 5,649,542 | 7/1997 | Archibald et al. | 128/681 |
| 5,720,292 | 2/1998 | Poliac | 128/672 |
| 5,722,414 | 3/1998 | Archibald et al. | 128/672 |
| 5,738,103 | 4/1998 | Poliac | 128/672 |
| 5,779,630 | * 7/1998 | Fein et al. | 600/323 |
| 5,797,850 | 8/1998 | Archibald et al. | 600/494 |
| 5,832,924 | 11/1998 | Archibald et al. | 128/672 |
| 5,857,976 | * 1/1999 | Quinn et al. | 600/526 |

* cited by examiner

Primary Examiner—Robert L. Nasser
(74) Attorney, Agent, or Firm—Kinney & Lange, P.A.

(57) ABSTRACT

The present invention is an improvement to a non-invasive blood pressure sensing device and method. The present invention is an improvement that includes a transducer with an associated memory or memories for storing data such as sensor characteristics and history information. In a preferred embodiment, the stored information includes transducer offsets and gains, date code, serial number, model type, usage counter, time stamp of the last test of the device, motor characteristics and one or more checksums. The stored data is used by the device for several purposes including calibration, generation of indications such as component expiration indications and test needed indications, automatic identification of appropriate algorithms for control and data manipulation, service and billing.

19 Claims, 10 Drawing Sheets

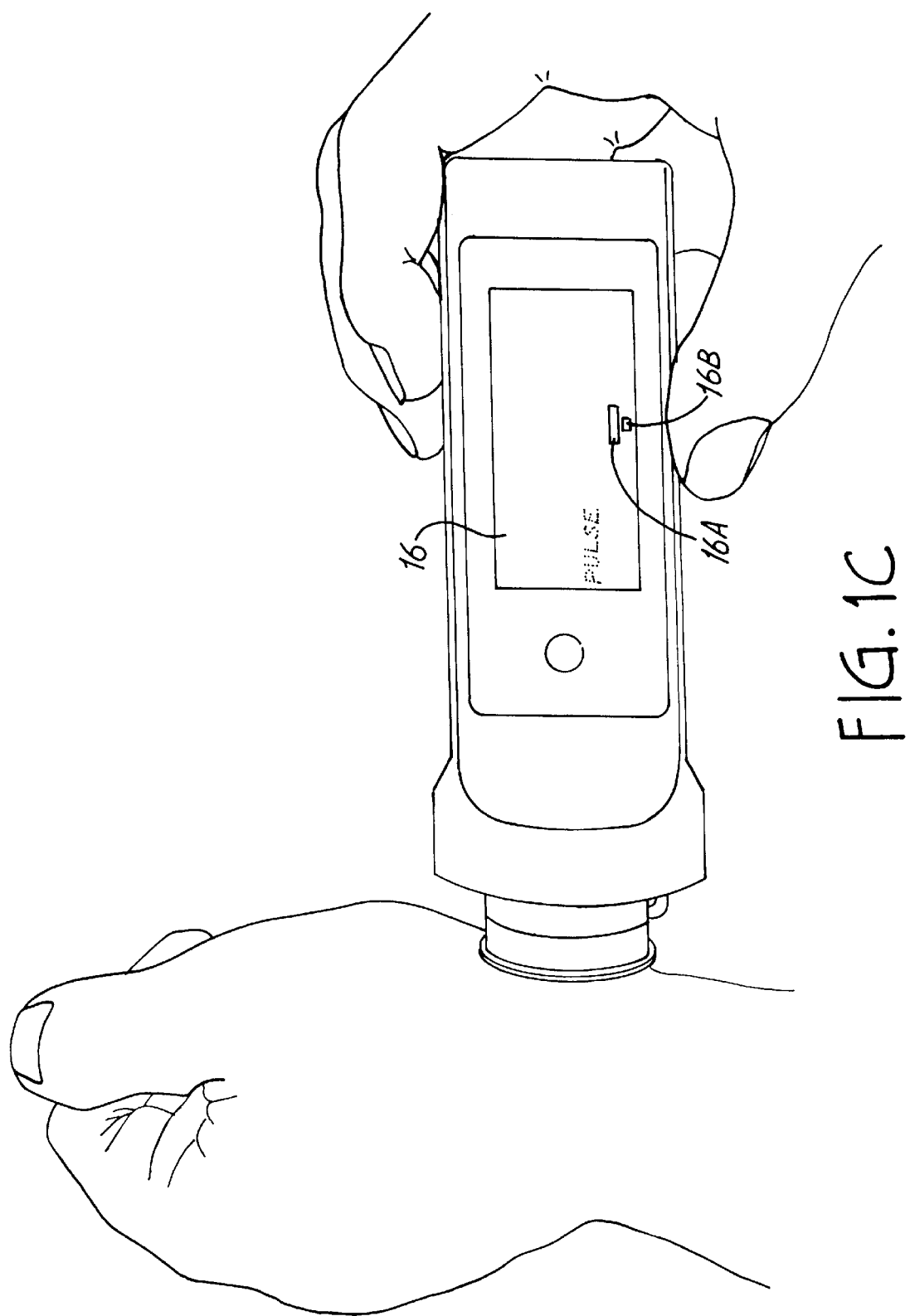

NON-INVASIVE BLOOD PRESSURE SENSING DEVICE AND METHOD USING TRANSDUCER WITH ASSOCIATE MEMORY

CROSS-REFERENCE TO RELATED APPLICATION(S)

None.

BACKGROUND OF THE INVENTION

The present invention relates to systems and devices for measuring arterial blood pressure. In particular, the invention relates to an improved method and device for measuring arterial blood pressure in a non-invasive manner using a transducer with an associated memory.

There has been a continuing need for devices which will measure blood pressure non-invasively, with accuracy comparable to invasive methods. Medwave, Inc. the assignee of the present invention, has developed non-invasive blood pressure measurement devices which are described in the following United States patents: U.S. Pat. No. 5,649,542 entitled CONTINUOUS NON-INVASIVE BLOOD PRESSURE MONITORING SYSTEM; U.S. Pat. No. 5,450,852 entitled CONTINUOUS NON-INVASIVE PRESSURE MONITORING SYSTEM; U.S. Pat. No. 5,640,964 entitled WRIST MOUNTED BLOOD PRESSURE SENSOR; U.S. Pat. No. 5,720,292 entitled BEAT ONSET DETECTOR; U.S. Pat. No. 5,738,103 entitled SEGMENTED ESTIMATION METHOD; U.S. Pat. No. 5,722,414 entitled CONTINUOUS NON-INVASIVE BLOOD PRESSURE MONITORING SYSTEM; U.S. Pat. No. 5,642,733 entitled BLOOD PRESSURE SENSOR LOCATOR; and U.S. Pat. No. 5,797,850 entitled METHOD AND APPARATUS FOR CALCULATING BLOOD PRESSURE OF AN ARTERY. Further description of these devices is found in U.S. patent application Ser. No. 08/912,139 filed Aug. 15, 1997, entitled HAND-HELD NON-INVASIVE BLOOD PRESSURE MEASUREMENT DEVICE, and U.S. patent application Ser. No. 09/299,222, filed Apr. 23, 1999, entitled BLOOD PRESSURE MEASUREMENT DEVICE WITH SENSOR LOCATOR.

As described in these patents and the pending patent applications, the Medwave non-invasive blood pressure measurement device and method determines blood pressure by sensing pressure waveform data derived from an artery. As varying pressure is applied to the artery by a sensing chamber, pressure waveforms are sensed by a transducer to produce sensed pressure waveform data. The varying pressure may be applied automatically in a predetermined pattern, or may be applied manually in a somewhat random fashion. The sensed pressure waveform data is analyzed to determine waveform parameters which relate to the shape of the sensed pressure waveforms. One or more blood pressure values are derived based upon the waveform parameters. The Medwave blood pressure measurement devices include both automated devices for continuously monitoring blood pressure (such as in a hospital setting) and hand-held devices which can be used by a physician, or by a patient when desired. These devices represent an important improvement in the field of non-invasive blood pressure measurement. Still further improvements, of course, are highly desirable.

BRIEF SUMMARY OF THE INVENTION

The present invention is an improvement to a non-invasive blood pressure sensing device and method. The present invention is an improvement that includes a transducer with an associated memory or memories for storing data such as sensor characteristics and history information. In a preferred embodiment, the stored information includes transducer offsets and gains, date code, serial number, model type, usage counter, time stamp of the last test of the device, motor characteristics and one or more checksums. The stored data is used by the device for several purposes including calibration, generation of status indications such as component expiration indications and test needed indications, automatic identification of appropriate algorithms for control and data manipulation, service and billing.

BRIEF DESCRIPTION OF THE DRAWINGS

FIGS. 1A–1D show the detail of the LCD display during a pressure measurement cycle.

DETAILED DESCRIPTION

Figure 1:
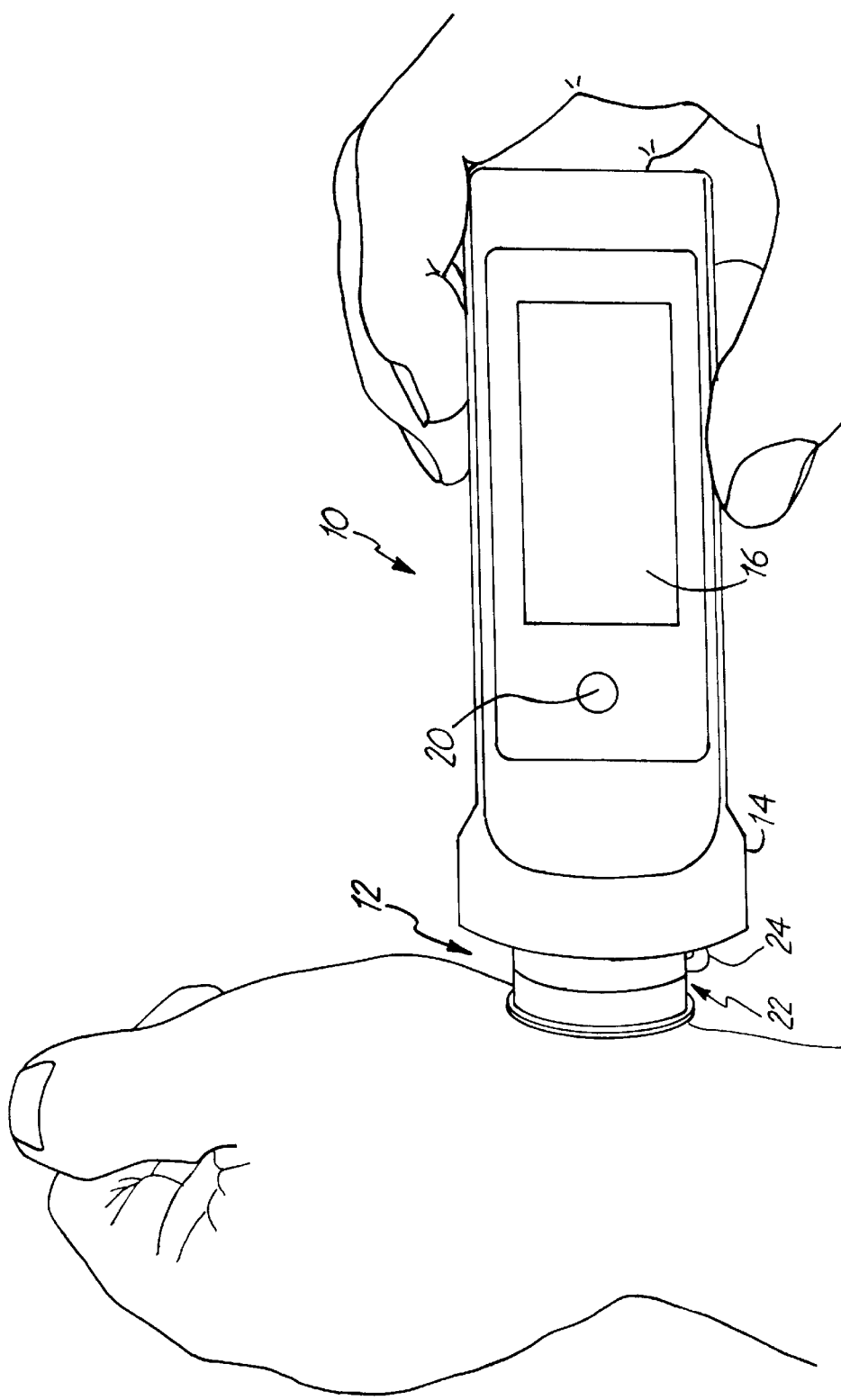
FIG. 1 is a perspective view of a blood pressure measuring device positioned over the wrist of a patient.
Figure 1A:
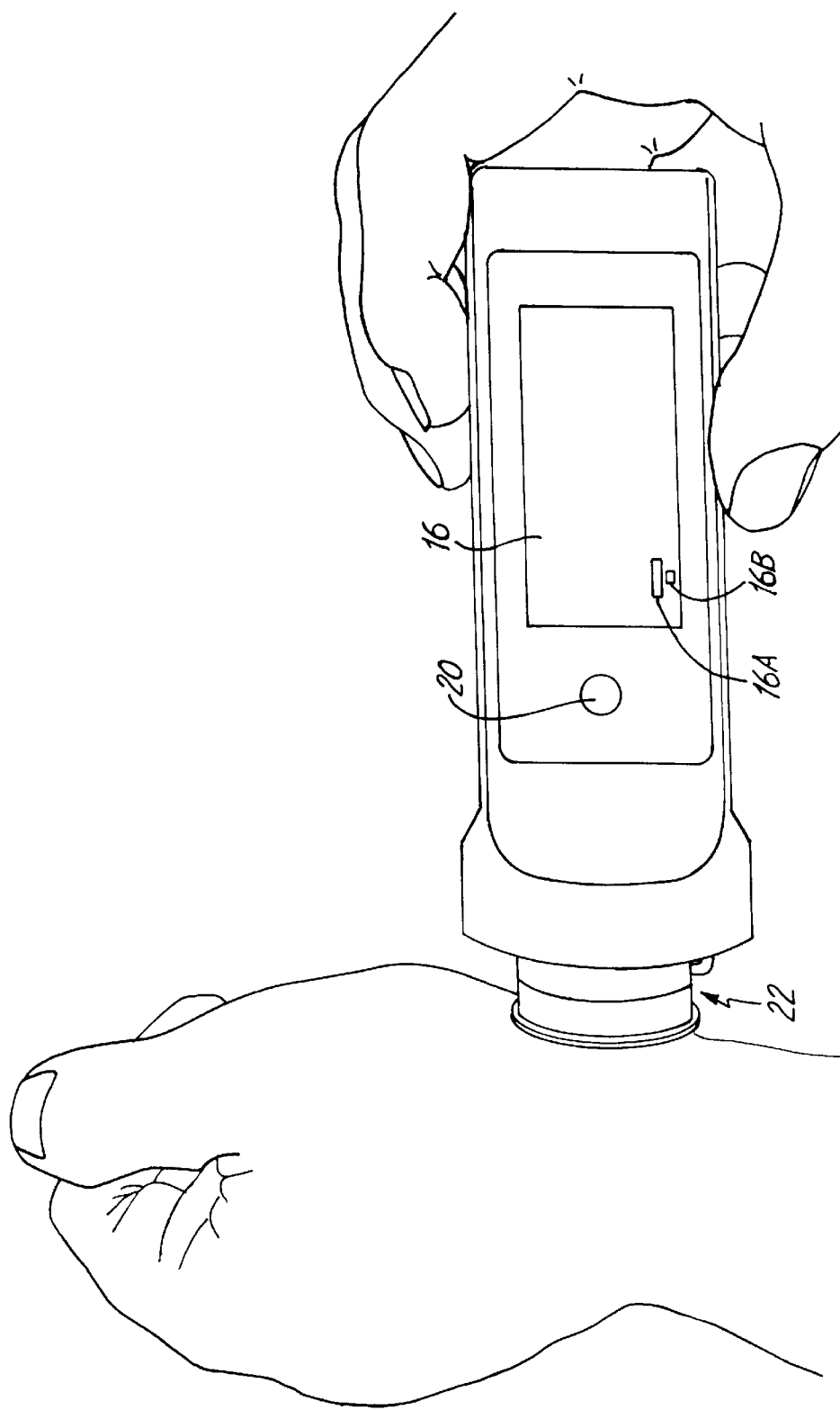

FIG. 1 illustrates a hand held blood pressure measurement device being used to measure and display blood pressure within an underlying artery within wrist 12 of a patient. With device 10, a small amount of force is manually applied to the radial artery at the projection of the styloid process bone. As the force is manually applied, blood pressure waveforms are recorded and the corresponding hold down pressure which is being manually applied is also recorded. Using the pressure shape of the blood pressure, waveform parameters are generated. These parameters, along with universal coefficients, are used to calculate pressure values which then can be displayed.

Blood pressure measurement device 10 includes main housing 14, display panel 16, on/off (power) and display select switch 20, sensor interface assembly 22, and connection plug 24.

Housing 14 contains all of the electrical components of measurement device 10. The diameter and length of housing 14 allow it to be easily held by the user (either medical personnel or the patient) during the measurement process. The hold down force is applied by applying force in an axial direction to wrist 12 which is transmitted from housing 14 to sensor interface assembly 22.

Display panel 16 is preferably a liquid crystal display (LCD). In a preferred embodiment, display panel 16 simultaneously displays the following values based upon blood pressure measurements: systolic pressure, diastolic pressure, pulse rate, and mean blood pressure. Display panel 16 also preferably provides visual prompting for manually applying a varying hold down pressure.

Power switch 20 is actuated to turn on power to the circuitry within housing 14. Timing circuitry within housing 14 automatically turns power off after a predetermined period of inactivity. Actuation of switch 20, after the unit is turned on, causes the display to indicate previous readings of blood pressure and pulse rate. In one embodiment there are ten memory locations for readings that can be displayed.

Sensor interface assembly 22 is pivotally mounted to housing 14. As pressure is manually applied by moving housing 14 toward the artery, that force is transferred from housing 14 to sensor interface assembly 22.

In operation, sensor interface assembly 22 is positioned over an artery such as the radial artery (as illustrated in FIG. 1). Alternatively, device 10 can be used in a number of other locations, such as on the temporal artery or the dorsalis pedis artery. The user then begins to apply force to the artery by applying axial force from housing 14 to sensor interface assembly 22. The force applied to the artery is swept in an increasing fashion so that pressure waveform data from a series of pulses are obtained with different amounts of force being applied. To achieve the desired pattern of variable force, user feedback is preferably provided with device 10.

In a preferred embodiment, feedback is in the form of audible tones and/or movable bars on display 16 as shown in FIGS. 1A–1D. Top bar 16A is a pacing bar controlled by the microprocessor. Bottom bar 16B moves in response to the hold down pressure the user applies to the wrist through sensor interface assembly 22. As pressure is applied, bar 16A moves at a fixed rate. The user causes bottom bar 16B to move at approximately the same rate as top bar 16A by applying a steadily increasing force.

The sequence of the measurement cycle is shown in FIGS. 1A–1D. First, the user presses power switch 20, which turns on the device 10. To take a reading, sensor interface assembly 22 is lightly pressed against a pulse locator (as illustrated in FIG. 1) so that bottom bar 16B remains under top bar 16A.

Top bar 16A will start to move across display screen 16. As top bar 16A starts to move, the user must apply increasing pressure through device 10 to the wrist so that bottom bar 16B tracks with the movement of top bar 16A.

Figure 1B:
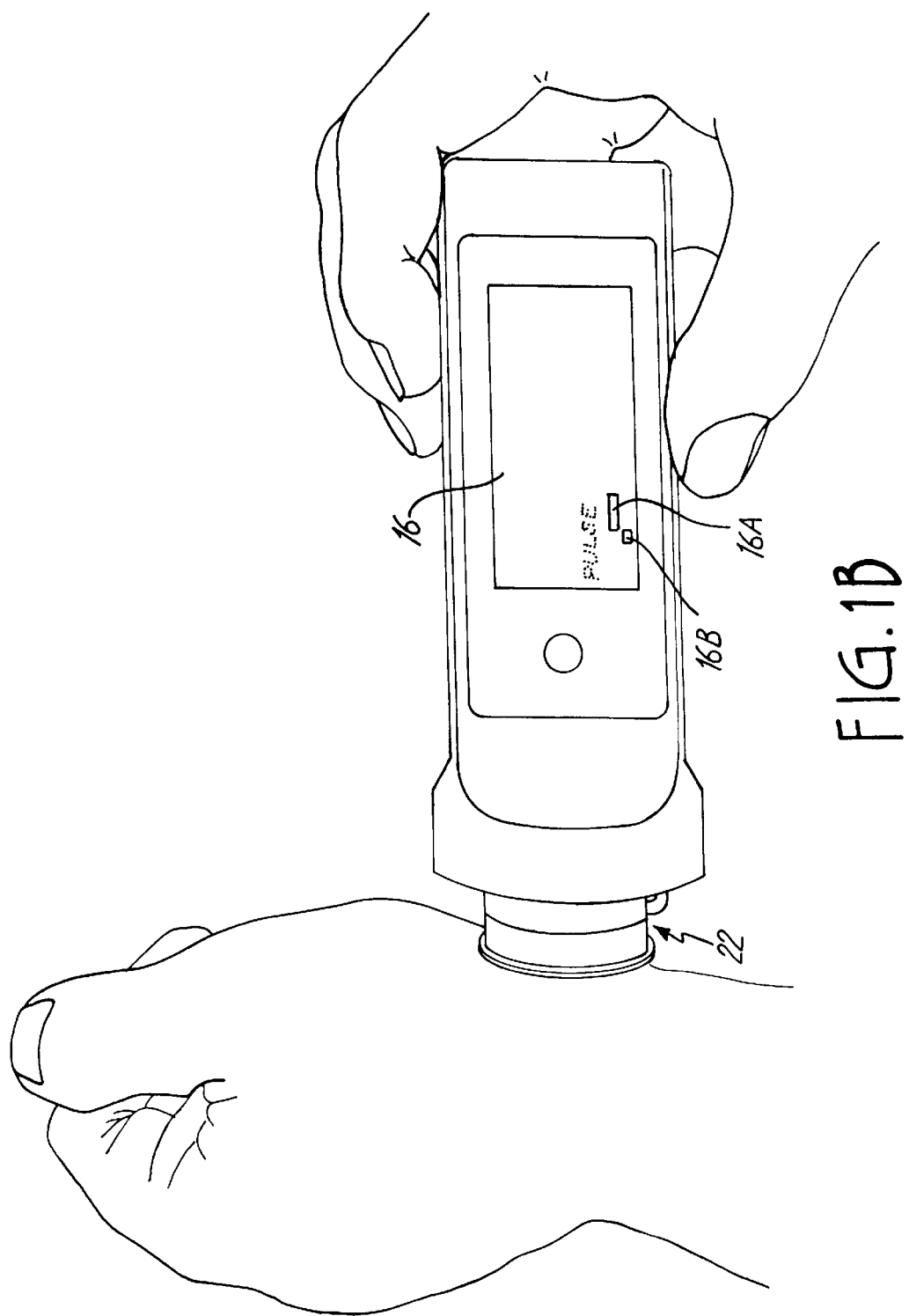

FIG. 1B shows display 16 as top bar 16A has started to move from left to right and bottom bar 16B has not yet begun to track the movement of top bar 16A. FIG. 1C shows bars 16A and 16B as the process continues. Both bars are continuing to move from left to right across the bottom of the display 16. The amount of force required to keep bottom bar 16B underneath top bar 16A will increase as top bar 16A moves across display 16 from left to right.

Figure 1D:
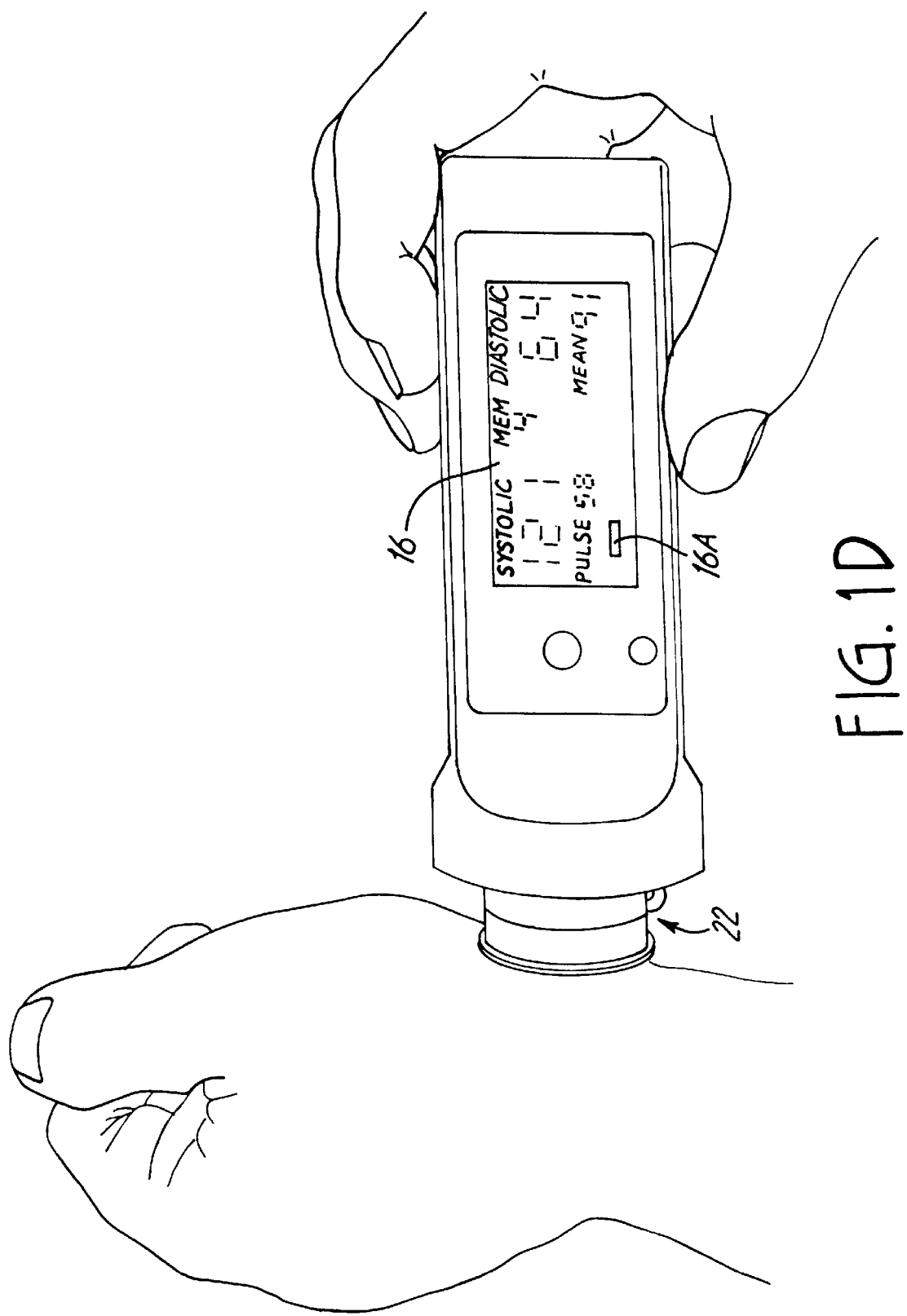

After a beep, the user can remove sensor interface assembly 22 from the wrist. At that point, top bar 16A returns to its left-most position, and bar 16B does not appear on the screen. This is shown in FIG. 1D. The user can then note the blood pressure reading. In a preferred embodiment illustrated in FIG. 1D, display 16 provides a digital readout of systolic, diastolic, and mean blood pressure, as well as pulse rate. An indication of memory location (by number) is also displayed.

As soon as the reading is complete, device 10 is ready to take another reading. There is no need to clear display 16. Device 10 stores a predetermined number of previous readings (such as the last 10 readings). To review prior readings, power switch 20 is pressed. This causes a different reading from memory to be displayed on display 16.

If a tone method is used as feedback, the user applies a force and each tone is modulated and has a higher pitch sound as the amplitude of the cardiac waveform increases. By listening to the tone, the user knows at what rate to apply the pressure to the artery. At the point of maximum energy transfer between the artery and sensor interface assembly 22, the cardiac pressure waveform reaches a peak amplitude and, therefore, the highest frequency tone is produced. As the user continues to apply higher pressure to the artery, the amplitude of the cardiac pressure waveform decreases, and therefore the frequency of the tone decreases. By listening to the tone, the user can perform a variable pressure sweep to measure pressure using device 10.

Feedback to the user can be supplied in other ways as well. For example, an audible tone can be produced using a combination of frequency modulation and amplitude modulation. In other words, as the amplitude of the pressure waveform increases, both pitch (frequency) and amplitude (volume or loudness) of the tone will change.

Figure 2:
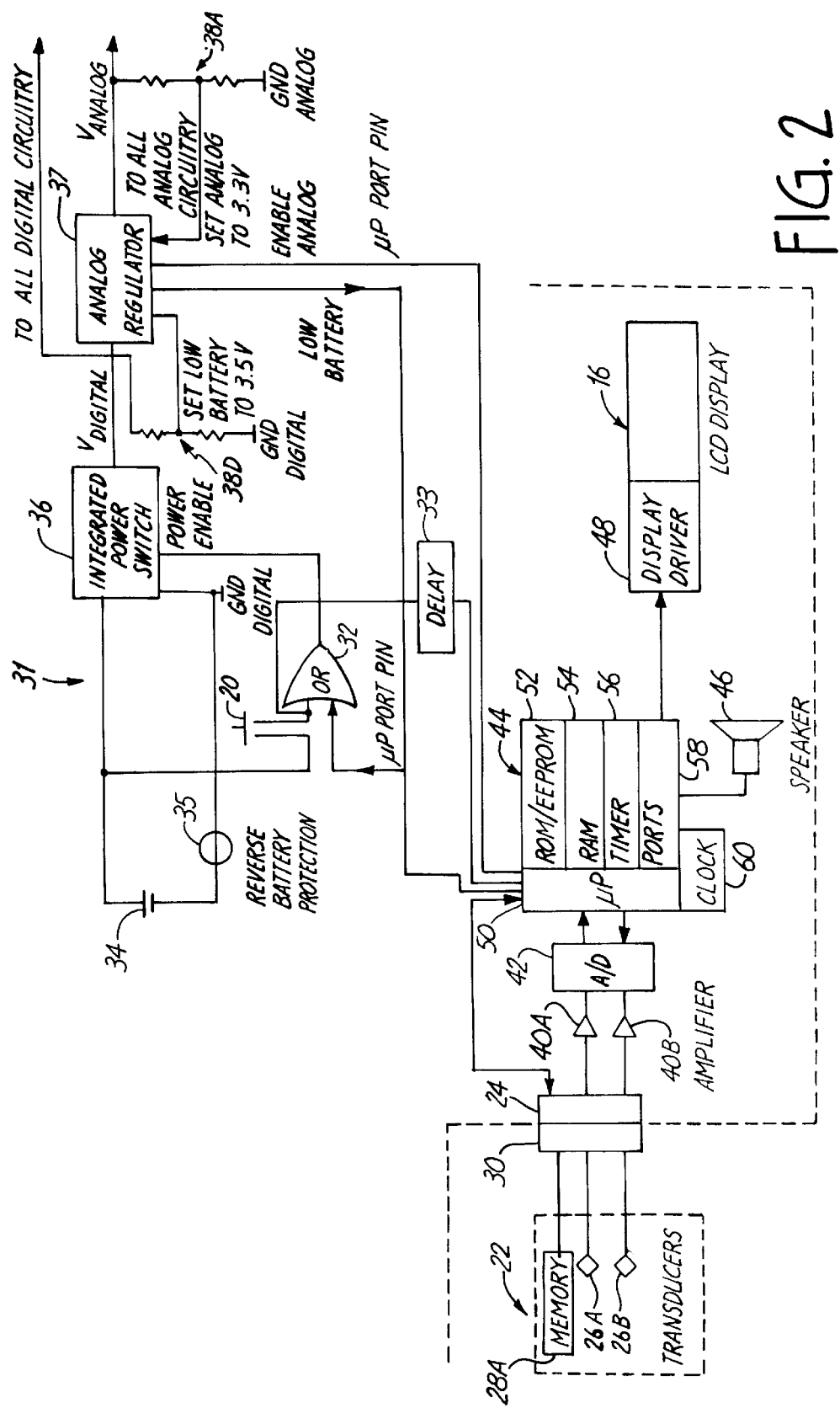
FIG. 2 is a block diagram of the blood pressure measuring device of FIG. 1.

FIG. 2 is an electrical block diagram of device 10. Pressure transducers 26A and 26B and nonvolatile memory 28A within sensor interface assembly 22 are connected through connector 30 and connector 24 to circuitry within housing 14. Power supply circuit 31 includes switch 20, OR circuit 32, delay circuit 33, battery 34, reverse battery protection 35, integrated power switch 36, analog regulator 37, and voltage dividers 38A and 38D. The output of analog regulator 37 is electrical power which is used to energize analog circuitry, which includes amplifiers 40A and 40B, and analog-to-digital (A/D) converter 42. Integrated power switch 36 supplies power to all digital circuits, which include microprocessor 44, speaker 46, display panel 16 and associated display drive and memory circuitry 48. Microprocessor 44 includes digital signal processing circuitry 50, read only memory (ROM) and electrically erasable programmable read only memory (EEPROM) 52, random access memory (RAM) 54, timer circuitry 56, input/output ports 58 and clock 60. A/D converter 42 may be integrated with microprocessor 44, while some of the memory may be external to microprocessor 44. Clock 60 provides the current day and date as well as the time.

Switch 20 is partially a monitoring pushbutton switch. Pressing switch 20 causes OR circuit 32 to turn on integrated power switch 36. Integrated power switch 36 supplies power to microprocessor 44, which in turn latches on OR circuit 32. The turn off of the circuit is controlled by microprocessor 44 discontinuing a signal to OR circuit 32. This occurs through a fixed time of no activity.

Transducers 26A and 26B sense pressure communicated within sensor interface assembly 22 and supply electrical signals to connector 30. In a preferred embodiment, transducers 26A and 26B are piezoresistive pressure transducers. Nonvolatile memory 28A is, in a preferred embodiment, an EEPROM. Memory 28A preferably has two sections—a permanent section which stores data permanently and does not allow the data to be erased or changed, and a read/write section which allows data to be erased, and new data to be stored while the device is operational.

In a preferred embodiment, the following data items are stored in the permanent section of memory 28A:

1. Transducer offsets (for both transducers 26A and 26B)
2. Transducer gains (for both transducers 26A and 26B)
3. Date code
4. Serial number
5. Model type
6. Checksum of above for validation The following data items are preferably stored in the read/write section of memory 28A:

1. Usage counter (hours or cycles)
2. Time stamp of last test of sensor

3. Checksum of above for validation

To obtain a data item from memory 28A, microprocessor 44 sends a request to memory 28A. When memory 28A receives a request, it locates the requested data and transmits it back to microprocessor 44. The received data is temporarily stored in RAM 54.

Memory 28A preferably stores at least one checksum for the stored data, so that the validity of the data can be verified. Microprocessor 44 verifies the validity of data received from memory 28A by calculating the checksum of the data and comparing the calculated checksum to the stored checksum. If the values are not the same, the data may be inaccurate.

Transducer offset and gain data for each transducer 26 are measured during the manufacturing process, and stored in the permanent section of memory 28A. All transducers typically have some inherent amount of error when they are first turned on. The amount of the error, or the transducer offset, is typically different for each transducer. Similarly, the transducer gain may vary from transducer to transducer. Application of a transducer gain is occasionally necessary because a transducer may not produce an accurate output for a given input or set of input values. In such cases, a transducer gain is applied so that the transducer produces an accurate output. By storing the transducer offset in memory 28A, the user does not have to go through the process of manually "zeroing" the offset. Rather, when device 10 is first powered up, microprocessor 44 sends a request to memory 28A, requesting the transducer offset for transducers 26A and 26B, obtains the requested information, and automatically makes the appropriate adjustments to eliminate the inherent error. Likewise, microprocessor 44 obtains the transducer gain data from memory 28A and makes appropriate adjustments to the data output by transducers 26 to ensure accuracy of the data.

Also during power-up, microprocessor 44 preferably interrogates memory 28A to obtain other device characteristics, including a date code, serial number, model type, usage counter, and time stamp. These and other data items may also be obtained at any time after power-up.

The date code may be used to identify an expiration date for transducers 26A and 26B. The first time sensor interface assembly 22 is used, microprocessor 44 loads an expiration date (or an initialization date) into memory 28A. Thereafter, each time device 10 is powered up, microprocessor 44 compares the date code received from memory 28A to the current day and date provided by clock 60, and determines whether the transducers 26 have expired. If the transducers have expired, an appropriate indication is provided on display 16 to inform the user of the expiration. Prior to expiration, a count-down indication may be provided on display 16 that informs the user the number of days remaining before expiration.

The model type and/or serial number may be used to indicate to microprocessor 44 which algorithms are to be applied to control sensor interface assembly 22 or to manipulate the data received from the sensor interface assembly 22. For example, a pediatric model may have characteristics that are different from an adult model requiring different algorithms or different control of the "squeezing" of the sensor on the wrist. As another example, a new model might have better noise rejection then a standard adult model and require a different algorithm to process the received information. In other embodiments, a third transducer may be used in certain model types requiring a different algorithm to process the additional information. RAM 54 or memory 52 stores the algorithms for each model type, and microprocessor 44 identifies the appropriate algorithms to use based on the model type and/or serial number obtained from memory 28A.

The usage counter stored in memory 28A indicates the number of times sensor interface assembly 22 has been used or the number of measurement cycles performed. Alternatively or additionally, the usage counter indicates the cumulative time of operation of sensor interface assembly 22. The usage counter is used for gathering long term data for billing, reliability and service. Usage data might be used for billing where a user is billed for usage of device 10, rather than paying a one time purchase price. Each time the sensor interface assembly 22 is used to take a reading from a patient, microprocessor 44 increments the usage counter and writes the new value to memory 28A. Microprocessor 44 may also use timer 56 or clock 60 to determine the amount of time sensor interface assembly 22 has been operated, and record this data in memory 28A. A variety of methods can be used to obtain the usage data for billing or service purposes. For example, if the usage counter passes a certain threshold, an indication may be generated on display 16 to indicate that device 10 should be serviced. Device 10 may also be coupled to a modem and interrogated with a remote computer, which would obtain the usage data and generate a bill based on the usage.

In a preferred embodiment, memory 28A stores a time stamp indicating the date and time of the last time device 10 was tested. Device 10 is tested by pressing a test button on the device. Test results may be displayed on display 16. Each time device 10 is tested, microprocessor 44 obtains the current date and time from clock 60 and writes the date and time data to memory 28A. If the time since the last test exceeds a predetermined threshold (e.g., 24 hours), microprocessor 44 preferably provides an indication on display 16, informing the user that device 10 should be tested.

The outputs of transducers 26A and 26B are analog electrical signals representative of sensed pressure. These signals are amplified by amplifiers 40A and 40B and applied to inputs of A/D converter 42. The analog signals to A/D converter 42 are converted to digital data and supplied to the digital signal processing circuitry 50 of microprocessor 44.

Based upon the pressure data received, microprocessor 44 performs calculations to determine blood pressure values. A preferred process of calculating blood pressure values is described in the previously mentioned Medwave patents and patent application, which are incorporated by reference. As each pulse produces a cardiac waveform, microprocessor 44 determines a peak amplitude of the waveform. Microprocessor 44 controls display driver 48 to create bars 16A and 16B of FIGS. 1A–1D or drives speaker 46 to produce audible tones which vary as a function of the hold down pressure. The moving bars or audible tones guide the user in applying a variable force to the artery.

When a measurement cycle has been completed, microprocessor 44 reorders the cardiac waveforms in increasing order of their corresponding hold down pressure and performs calculations to determine systolic pressure, diastolic pressure, mean blood pressure, and pulse rate. These values are displayed as shown in FIG. 1D. If switch 20 is pressed while microprocessor 44 is on, a signal is supplied through delay circuit 33 to microprocessor 44, causing it to toggle to a new pressure reading. The memory location of that pressure reading is also displayed, as shown in FIG. 1D.

Figure 3A:
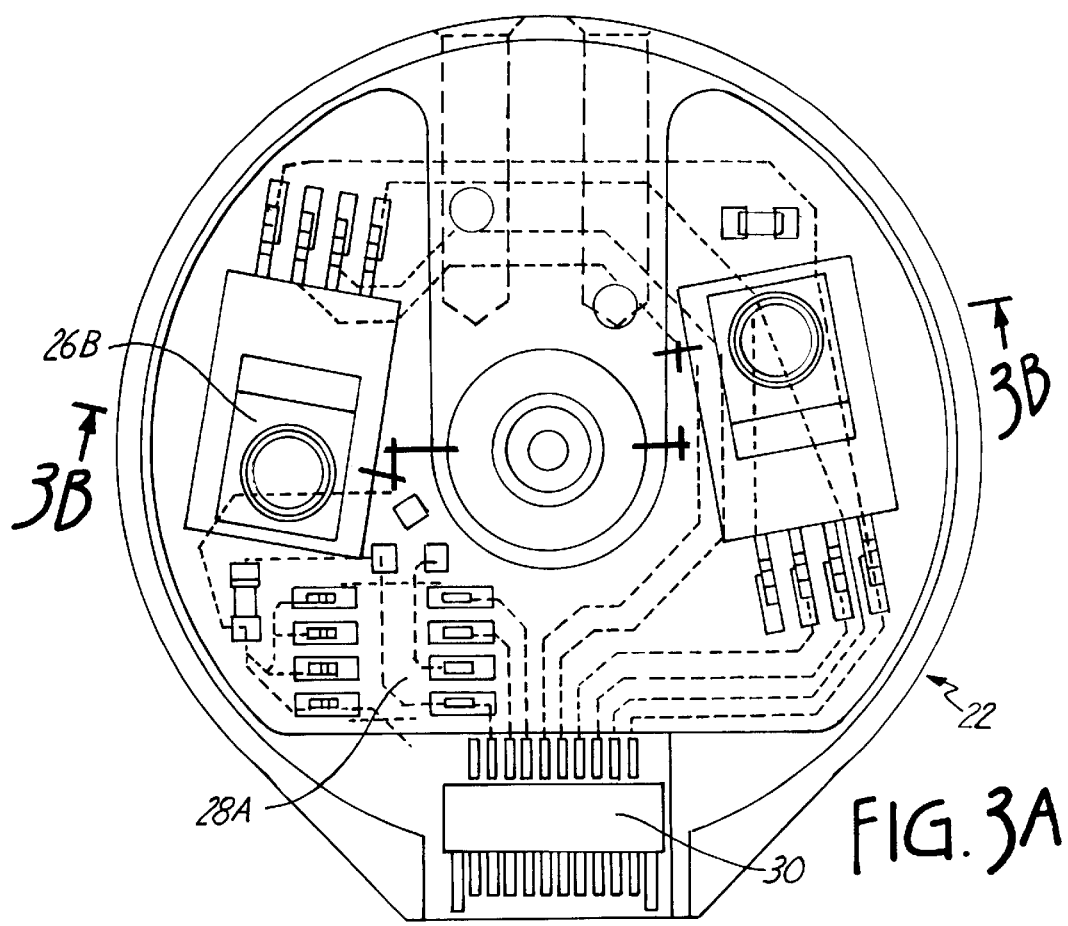
FIG. 3A is a top view of the sensor interface assembly.
Figure 3B:
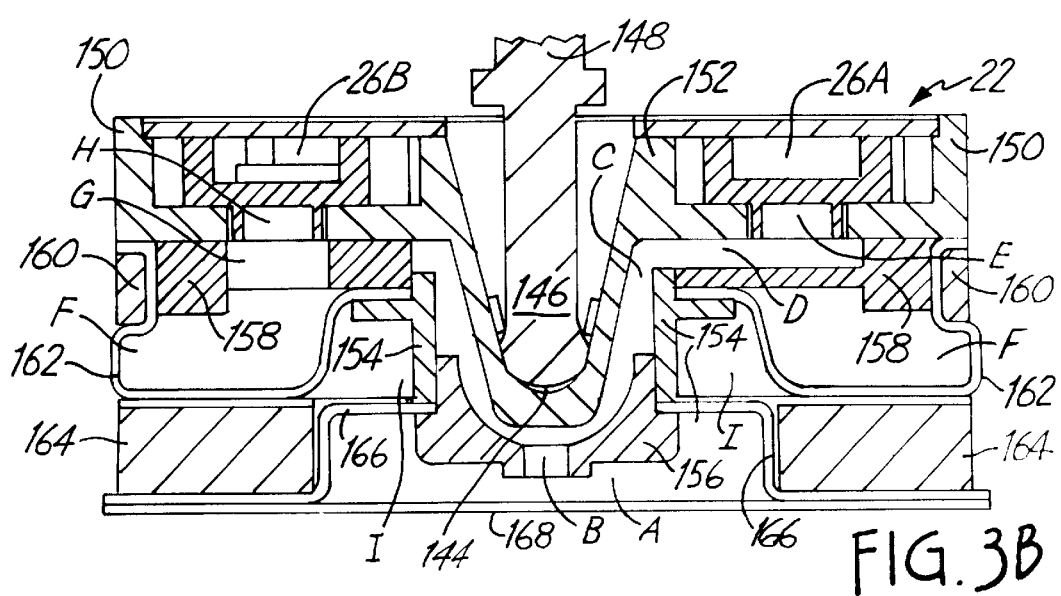
FIG. 3B is a cross-sectional view of the sensor interface assembly along section 3B—3B of FIG. 3A.

FIGS. 3A and 3B illustrate sensor interface assembly 22 in detail. Sensor interface assembly 22 includes top plate 150, upper cup 152, upper capture 154, diaphragm capture 156, inner mounting ring 158, outer mounting ring 160, side wall diaphragm 162, damping ring 164, inner diaphragm 166, and outer diaphragm 168.

As shown in FIG. 3B, transducer 26A measures fluid pressure in fluid-filled sensor chamber A. Channels B, C, D, and E provide fluid pressure communications between transducer 26A and sensor chamber A. Transducer 26B measures fluid pressure in fluid-filled ring chamber F. Channels G and H provide fluid pressure communications between transducer 26B and ring chamber B. Connector 30 communicates with transducers 26A and 26B and non-volatile memory 28A.

FIG. 3B also shows how the sensor interface assembly 22 is pivotally connected to housing 14 by a ball 146 and socket 144 arrangement. The ball 146 is pivotally mounted in socket 144. Ball 146 is pivotally mounted in socket 144. Because sensor interface assembly 22 is pivotally coupled to stem 148 about a low pivot point. This permits sensor interface assembly 22 to be stably positioned above the underlying artery. In addition, the low pivot point enables the user to apply a more direct, uniform force on outer diaphragm 168. Thus, the hold down pressure manually applied by the user (through housing 14 and stem 148) is more uniformly applied to the anatomy above the underlying artery.

Side wall diaphragm 162 and rings 158 and 160 define annular deformable ring chamber F coupled to ring 164. Side wall diaphragm 162 is preferably formed from a generally circular sheet of flexible material, such as polyurethane, and is filled with fluid. Diaphragm 162 has a hole sized to fit around the upper portion of upper capture 154. The outer edge portion of diaphragm 162 is trapped and held between outer ring 160 and top plate 150. The inner edge portion of diaphragm 162 is trapped and supported between ring 158 and upper capture 154. Diaphragm 162 is made from a flexible material and is bulged outward when ring chamber F is filled with fluid. Ring chamber F is compressible and expandable in the vertical direction so as to be able to conform to the anatomy of the patient surrounding the underlying artery. As a result, the distance between top plate 150 and the patient's anatomy can vary around the periphery of side wall diaphragm 162 according to the contour of the patient's anatomy. Furthermore, because fluid is permitted to flow through and around chamber F, pressure is equalized around the patient's anatomy.

Damping ring 164 generally consists of an annular compressible ring and is preferably formed from a foam rubber or other pulse dampening material such as open celled foam or closed cell foam. Ring 164 is centered about and positioned between side wall diaphragm 162 and diaphragms 166 and 168. Damping ring 164 is isolated from the fluid coupling medium within sensor chamber A. Because ring 164 is formed from a compressible material, ring 164 absorbs and dampens forces in a direction parallel to the underlying artery which are exerted by the blood pressure pulses on sensor interface assembly 22 as the blood pressure pulse crosses sensor interface assembly 22. Because bottom ring 164 is isolated from the fluid coupling medium in sensor chamber A, the forces absorbed or received by ring 164 cannot be transmitted to the fluid coupling medium. Instead, these forces are transmitted across ring 164 and side wall diaphragm 162 to top plate 150. Because this path is distinct and separate from the fluid coupling medium, sensor chamber A and the fluid coupling medium are isolated from these forces. In addition, ring 164 also presses tissue surrounding the artery to neutralize or offset forces exerted by the tissue.

Upper diaphragm 166 is an annular sheet of flexible material having an inner diameter sized to fit around diaphragm capture 156. An inner portion of upper diaphragm 166 is trapped or captured (and preferably adhesively affixed) between the lip of diaphragm capture 156 and the bottom rim of upper capture 154.

The intermediate portion of upper diaphragm 166 is adjacent to expansion cavity I and is isolated from ring 164 and ring chamber F. Upper diaphragm 166 is permitted to initially move upward into expansion cavity I as ring chamber F, ring 164, and outer diaphragm 168 conform to the anatomy of the patient surrounding the underlying artery. As ring 164 is pressed against the anatomy of the patient surrounding the artery to neutralize or offset forces exerted by the tissue, outer diaphragm 168 is also pressed against the anatomy and the artery. However, because upper diaphragm 166 is permitted to roll into expansion cavity I, sensor chamber A does not experience a large volume decrease and a large corresponding pressure increase. Thus, sensor interface assembly 22 permits greater force to be applied to the anatomy of the patient through ring 164 to neutralize tissue surrounding the artery without causing a corresponding large change in pressure within sensor chamber A as the height of the side wall changes. As a result, sensor interface assembly 22 achieves more consistent and accurate blood pressure measurements.

Outer diaphragm 168 is a generally circular sheet of flexible material capable of transmitting forces from an outer surface to fluid within sensor chamber A. Outer diaphragm 168 is coupled to inner diaphragm 166 and is configured for being positioned over the anatomy of the patient above the underlying artery. Outer diaphragm sheet 168 includes non-active portion or skirt and an active central portion. The skirt constitutes the area of diaphragm 168 where inner diaphragm 166 is heat sealed or bonded to outer diaphragm 168.

The active portion of outer diaphragm 168 is not bonded to inner diaphragm 166, and is positioned below and within the inner diameter of ring 164. The active portion of outer diaphragm 168 is the active area of sensor interface assembly 22 which receives and transmits pulse pressure to transducer 26A.

The coupling medium within sensor chamber A and passages B–E may consist of any fluid (gas or liquid) capable of transmitting pressure from diaphragm 168 to transducer 26A. The fluid coupling medium interfaces between the active portion of outer diaphragm 168 and transducer 26A to transmit blood pressure pulses to transducer 26A. Because the fluid coupling medium is contained within sensor chamber A and passages B–E, which are isolated from the side wall of sensor interface assembly 22, the fluid coupling medium does not transmit blood pressure pulses parallel to the underlying artery, forces from the tissue surrounding the underlying artery and other forces absorbed by the side wall to transducer 26A. Forces parallel to the underlying artery are dampened by the compressible material of ring 164. As a result, sensor interface assembly 22 more accurately measures and detects arterial blood pressure.

Sensor interface assembly 22 provides external measurements of blood pressure in an underlying artery. Because sensor interface assembly 22 senses blood pressure non-invasively, blood pressure is measured at a lower cost and without medical risks. Because sensor interface assembly 22 is relatively small compared to the larger cuffs used with oscillometric and auscultatory methods, sensor interface assembly 22 applies a hold down pressure to only a relatively small area above the underlying artery of the patient. Consequently, blood pressure measurements may be taken with less discomfort to the patient. Because sensor interface assembly 22 does not require inflation or deflation, faster, more frequent measurements may be taken.

Furthermore, sensor interface assembly 22 better conforms to the anatomy of the patient so as to be more comfortable to the patient and so as to achieve more consistent and accurate blood pressure measurements. Because ring chamber F is deformable and filled with fluid, ring chamber F better conforms to the anatomy of the patient and equalizes pressure applied to the patient's anatomy. Because ring 164 is compressible and because outer diaphragm 168 is flexible and is permitted to bow or deform inwardly, ring 164 and outer diaphragm 168 also better conform to the anatomy of the patient. At the same time, however, sensor interface assembly 22 does not experience a large sudden increase in pressure in sensor chamber A as ring 164 and outer diaphragm 168 are pressed against the anatomy of the patient. Ring chamber F and ring 164 apply force to the anatomy of the patient to neutralize the forces exerted by tissue surrounding the underlying artery. Because ring chamber F and ring 164 are both compressible in height, the height of the side wall decreases as the side wall is pressed against the patient. Diaphragms 166 and 168 are also conformable. However, because the intermediate portion of inner diaphragm 166 is permitted to move upward into expansion cavity I, sensor chamber A does not experience a large volume decrease and a corresponding large pressure increase. Thus, the side wall is able to apply a greater force to the anatomy of the patient without causing a corresponding large, error-producing increase in pressure within sensor chamber A due to the change in height of the side wall and the change in shape of outer diaphragm 168.

At the same time, sensor interface assembly 22 permits accurate and consistent calculation of blood pressure. Because of the large sensing area through which blood pressure pulses may be transmitted to transducer 26A, sensor interface assembly 22 is not as dependent upon accurate positioning of the active portion of outer diaphragm 168 over the underlying artery. Thus, sensor interface assembly 22 is more tolerant to patient movement as measurements are being taken.

Moreover, sensor interface assembly 22 achieves a zero pressure gradient across the active face of the sensor, achieves a zero pressure gradient between the transducer and the underlying artery, attenuates or dampens pressure pulses that are parallel to the sensing surface of the sensor, and neutralizes forces of the tissue surrounding the underlying artery. Sensor interface assembly 22 contacts and applies force to the anatomy of the patient across the skirt and the active portion of outer diaphragm 168. However, the pressure within sensor chamber A is substantially equal to the pressure applied across the active portion of outer diaphragm 168. The remaining force applied by sensor interface assembly 22 across the skirt, which neutralizes or offsets forces exerted by the tissue surrounding the underlying artery, is transferred through the side wall (ring 164 and ring chamber F) to top plate 150. As a result, the geometry and construction of sensor interface assembly 22 provides the proper ratio of pressures between the skirt and the active portion of outer diaphragm 168 to neutralize tissue surrounding the underlying artery and to accurately measure the blood pressure of the artery. In addition, because the fluid coupling medium within sensor chamber A is isolated from the side wall, pressure pulses parallel to the underlying artery, forces from tissue surrounding the underlying artery, and other forces absorbed by the side wall are not transmitted through the fluid coupling medium to transducer 26A. Consequently, sensor interface assembly 22 also achieves a zero pressure gradient between transducer 26A and the underlying artery.

Blood pressure measuring device 10 determines blood pressure values from the sensed waveform pressure amplitudes sensed by sensor interface assembly 22 and from other parameters derived from the pressure amplitudes using a stored set of coefficients. A pressure amplitude is determined at each sample point.

Figure 4:
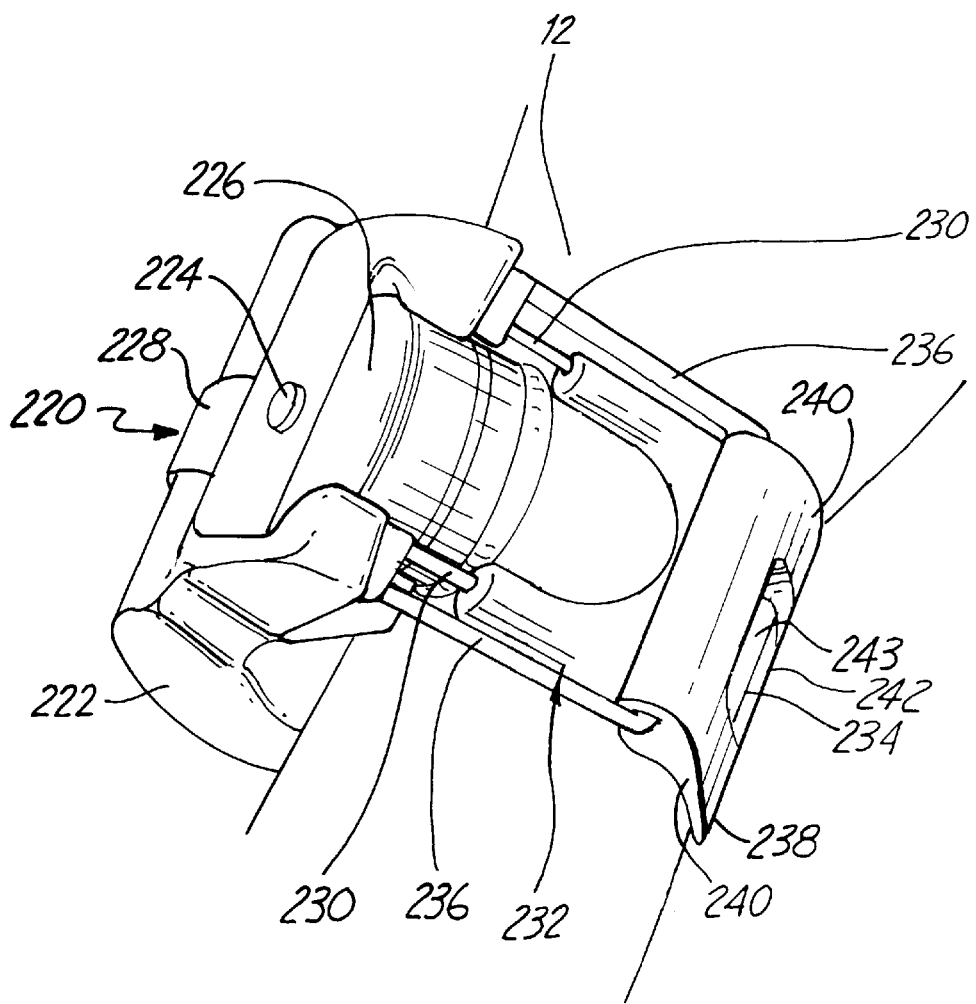
FIG. 4 ia a perspective view of a preferred embodiment of a continual blood pressure measurement device positioned over the wrist of a patient.

FIG. 4 illustrates a continual blood pressure measurement device 220, which is another preferred embodiment that uses a transducer with associated memory for storing data such as sensor characteristics and history information. The continual blood pressure measurement device 220 is shown being used to measure blood pressure within an underlying artery within wrist 12 of a patient. Measurement device 220 includes holddown assembly 222, swivel mount 224, sensor interface assembly 226, electrical connector 228, slide pins 230, sensor locator 232, and wrist mount 234. Holddown assembly 222 includes cable 236 and swivel 238. Sensor locator 232 includes locator fingers 240 and locator pad 242.

A continual blood pressure device without the locator feature is substantially disclosed in U.S. patent application Ser. No. 08/388,752 entitled WRIST MOUNTED BLOOD PRESSURE SENSOR (herein incorporated by reference) and assigned to Medwave, Inc. Generally, holddown assembly 222 causes sensor interface assembly 226 to apply varying pressure to the underlying artery of wrist 12. Holddown assembly 222 also regulates the tightness of wrist mount 234 about wrist 12 to control the holddown pressure and to prevent constriction of blood flow through wrist 12. Sensor interface assembly 226 interfaces between the underlying artery and a sensor (not shown) such as a transducer to calculate the blood pressure of the underlying artery based upon signals produced by the measurement device 220. Sensor interface assembly 226 is pivotally connected to holddown assembly 222 via swivel mount 224. Swivel mount 224 allows sensor interface assembly 226 to pivot near the wrist surface to accommodate the anatomy of a patient.

Holddown assembly 222 and wrist mount 234 maintain measurement device 220 on wrist 12 of the patient. Wrist mount 234 loops around swivel 238 and is tightened around wrist 12 until sensor interface assembly 226 contacts the anatomy of the patient. Holddown assembly 222 causes interface assembly 226 to apply pressure upon the underlying artery by articulation of cable 236 into holddown assembly 222. As cable 236 is drawn into holddown assembly 222, swivel 238 is pulled toward holddown assembly 222 and wrist mount 234 is tightened. The articulation of cable 236 and resultant tightening of wrist mount 234 causes sensor interface assembly 226 to apply a force on the underlying radial artery. Holddown assembly 222 controls the rate and amount of articulation of cable 236 and thus controls the amount and rate of the varying pressure.

In the preferred embodiment of the continual blood pressure measurement device, cable 236 includes an inner string covered in part by flexible tubing. Preferably the inner string enters holddown assembly 222 and is wound around a wind-up shaft (not shown). The wind-up shaft is controlled by motor assembly 260 (shown in FIG. 6) contained in holddown assembly 222. Cable 236 is articulated by the motor assembly spinning the wind-up shaft and winding the inner string. As the inner string winds around the wind-up shaft and cable 236 is drawn into holddown assembly 222, the length of the exposed inner string of cable 236 outside of holddown assembly 222 is shortened and wrist mount 234 is tightened. Flexible tubing of cable 236 is preferably long enough to cover the exposed portion of the inner string of cable 236 outside of holddown assembly 222. Preferably, the flexible tubing of cable 236 extends into holddown assembly 222, but is not long enough to be wound around the wind-up shaft. The flexible tubing of cable 236 provides durability to cable 236 which incurs significant stress during the continual measurement process.

Electrical connection 228 electrically couples sensor interface assembly 226 with holddown assembly 222. Additionally, power for the sensor (not shown) such as a transducer, within sensor interface assembly 226 is delivered via electrical connection 228. Blood pressure waveform signals produced by sensor interface assembly 226 are communicated to external control and display device 280 (shown in FIG. 6) using electrical connection 228.

Sensor locator 232 positions measurement device 220 so that sensor interface assembly 226 lies directly over the radial artery running along the styloid process bone within wrist 12 of a patient. Sensor locator 232 is preferably a U-shaped member defined by the integral mold of locator pad 242 and locator fingers 240. Locator fingers 240 are cylindrical extensions with distal ends that extend toward locator pad 242. Locator fingers 240 and locator pad 242 are integrally formed so that locator pad 242 forms a distal extension of locator fingers 240 that bridges locator fingers 240. The U-shaped sensor locator 232 forms gap 243 between locator fingers 240.

In operation, gap 243 of sensor locator 232 is positioned over the protrusion of the styloid process bone with locator fingers 240 straddling the styloid process bone. Positioning sensor locator 232 over the styloid process bone causes sensor interfaces assembly 226 to be properly positioned over the underlying radial artery for accurate blood pressure measurement.

Sensor locator 232 is slidably connected to holddown assembly 222 via slide pins 230. Slide pins 230 are fixedly connected to holddown assembly 222, while being slidably coupled to locator fingers 240 of sensor locator 232. Each locator finger 240 includes a bore for receiving one of slide pins 230. As pressure is applied to the underlying artery (as cable 236 is drawn into holddown assembly 222 and wrist mount 234 tightened), sensor locator 232 maintains its position, straddling the protrusion of the styloid process bone, by allowing slide pins 230 to slide into the respective bores of locator fingers 240.

Figure 5:
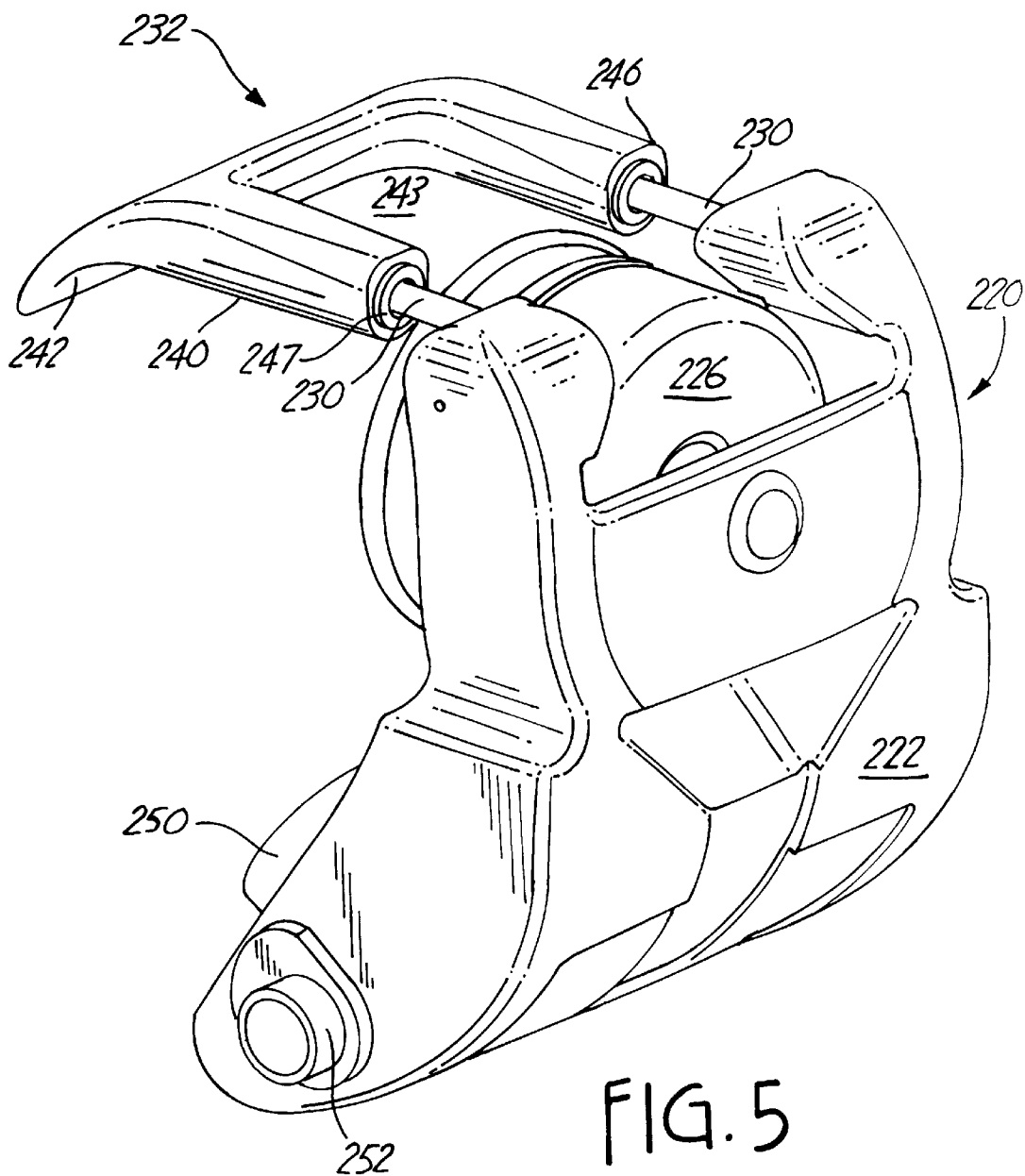
FIG. 5 is a perspective view of the continual blood pressure measurement device of FIG. 4 with certain hold-down portions removed.

FIG. 5 shows continual blood pressure measurement device 220 with portions of holddown assembly 222 including cable 236 removed to better illustrate sensor locator 232. As is more clearly shown in FIG. 5, in addition to locator fingers 240, locator pad 242, and gap 243, sensor locator 232 also includes slide pin connectors 246 and 247. FIG. 5 also illustrates that measurement device 220 additionally includes wrist pads 250 (only a single wrist pad is shown) and electrical connector 252.

Locator pad 242 is preferably curved at its digital end to more securely contact a patient's anatomy. Additionally, locator pad 242 consists preferably of flexible rubber. A flexible locator pad 242 is more comfortable to a patient and better accommodates the varying anatomies of patients. As can be better seen in FIG. 5, locator fingers 240 include slide pin connectors 246 and 247. Slide pin connectors 246 and 247 are press fit into the respective bores of locator fingers 240. Slide pin connectors 246 and 247 slidably receive slide pins 230. Preferably, slide pin connectors 246 and 247 are spring biased to maintain sensor locator 232 separated from holddown assembly 222.

Wrist pads 250 are configured for being positioned over and proximate to a surface of wrist 12. Wrist pads 250 support measurement device 220 adjacent to wrist 12 and provide additional comfort to a patient. Electrical connector 252 allows continual blood pressure measurement device 220 to communicate with external control and display device 280 (shown in FIG. 6). The control device 280 instructs measurement device 220, via electrical connector 252, to begin the measurement process and controls the applied holddown pressure. Furthermore, external control and display device 280 receives the sensed blood pressure waveform signals via electrical connector 252 and records, processes and displays those signals as well as the systolic, mean, and diastolic blood pressures and a pulse rate.

Figure 6:
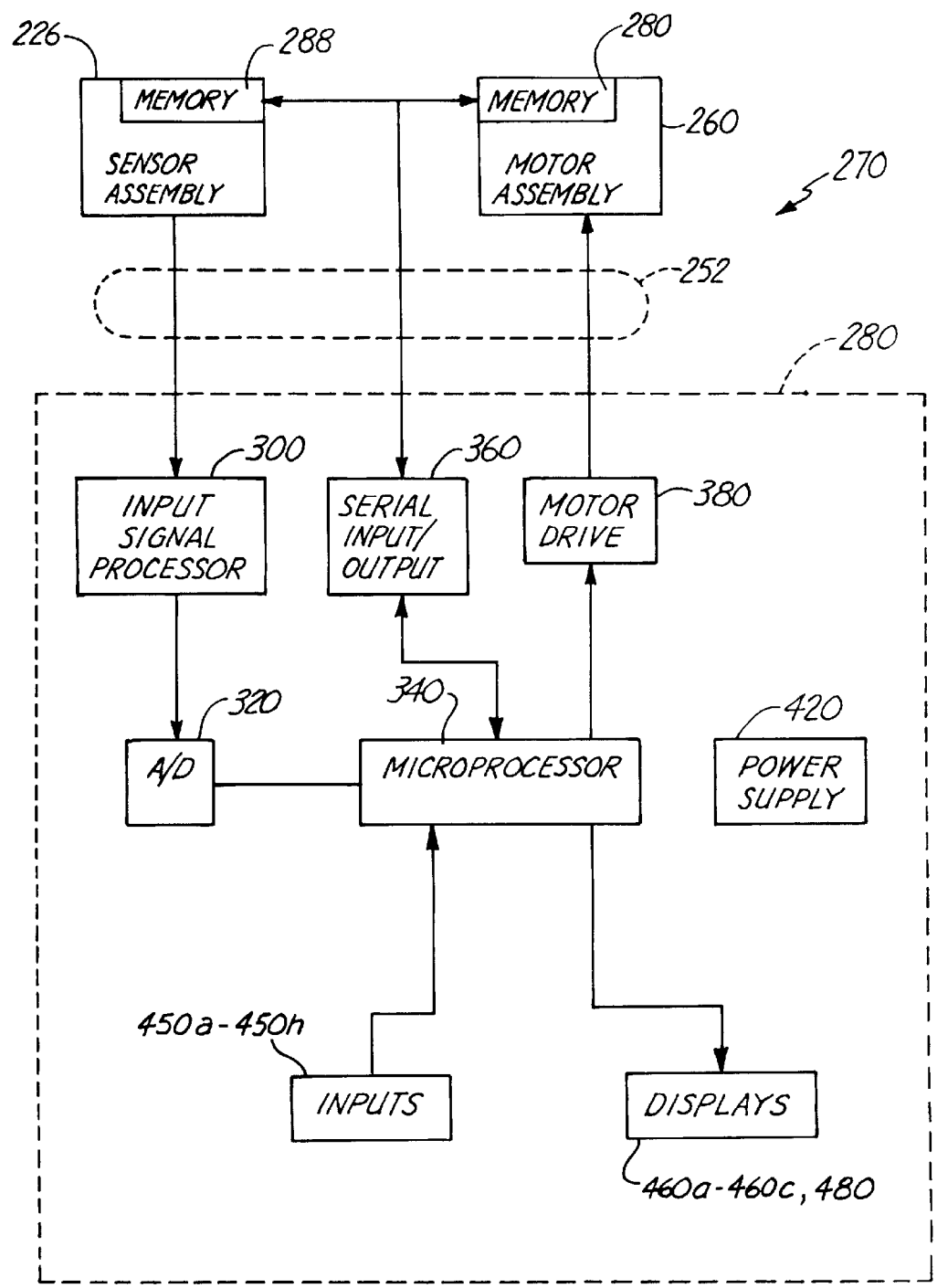
FIG. 6 is a block diagram of a continual blood pressure monitoring system.

FIG. 6 shows a block diagram of continual blood pressure monitoring system 270. Monitoring system 270 includes sensor interface assembly 226, motor assembly 260 and control and display device 280. Sensor interface assembly 226 and motor assembly 260 are included within measurement device 220 (shown in FIGS. 4 and 5). Control and display device 280 is electrically coupled to sensor interface assembly 226 and motor assembly 260 via electrical connector 252. Control and display device 280 includes input signal processor 300, analog-to-digital converter 320, microprocessor 340, serial input/output interface 360, motor drive 380, power supply 420, inputs 450a–450h, and displays 460a–460c and 480. In operation, microprocessor 340 receives inputted signals from inputs 450a–450h. Inputs 450a–450h may also consist of a keyboard or other input mechanisms. Inputs 450a–450h permit microprocessor 340 to be tested and calibrated.

Microprocessor 340 controls motor drive 380 to vary hold down pressure applied by motor assembly 260 on sensor interface assembly 226. Hold down pressure is applied to the anatomy of the patient directly above the artery by sensor interface assembly 226. The hold down pressure applied by motor assembly 260 on sensor interface assembly 226 is increased over time. As the force or hold down pressure applied by sensor interface assembly 226 increases, the amplitude of the blood pressure pulse also increases until a maximum amplitude results. Once the maximum amplitude or maximum energy transfer results, the amplitude of the blood pressure pulse begins to decrease as the artery begins to flatten out beyond the point of maximum energy transfer.

Sensor interface assembly 226 senses and detects the amplitude and shape of the blood pressure pulses within the underlying artery. Sensor interface assembly 226 creates electric sensor signals representing the amplitude of the sensed blood pressure pulses. The sensor signals are transmitted to input signal processor 300 of control and display device 280. Input signal processor 300 processes the sensor signals and filters any unwanted or undesirable noise and other effects. The sensor signals are then transmitted from input signal processor 300 to analog-to-digital converter 320. Analog-to-digital converter 320 converts the sensor signal into digital form. A digital signal representing the amplitude of the sensed blood pressure pulses is sent to microprocessor 340.

Based upon the digital sensor signals representing the sensed amplitude and shape of the blood pressure pulses, microprocessor 340 determines wave shape information by measuring amplitude and shape versus time of individual cardiac cycles. The arterial wave shape information is determined by sampling the arterial waves at a rate significantly above heart rate so that a good definition of the arterial pressure wave is measured. From this information, microprocessor 340 calculates systolic, diastolic and mean blood pressures. The calculated blood pressures are displayed on displays 460a–460c. Power supply 420 provides power to display device 280 and motor assembly 260.

Sensor interface assembly 226 includes non-volatile memory 28B, and motor assembly 260 includes non-volatile memory 28C. Like memory 28A shown in FIG. 2, memories 28B and 28C are EEPROMs that preferably include two sections—a permanent section which stores data permanently and does not allow the data to be erased or changed, and a read/write section which allows data to be erased, and new data to be stored while the device is operational. Memories 28B and 28C preferably store the same types of data items as memory 28A, such as transducer offsets and gains, date code, serial number, model type, usage counter, time stamp of the last test of the sensor, and one or more checksums.

The data stored in memories 28B and 28C is accessed in a manner similar to that for memory 28A. To obtain a data item from memory 28B or 28C, microprocessor 340 sends a request to serial input/output interface 360, which then passes the request to memories 28B and 28C over a serial communication link. Serial input/output interface 360 acts as a buffer between memories 28B–28C and microprocessor 340. Memories 28B and 28C preferably share the same serial data lines to minimize the number of wires used. The appropriate memory 28B-28C responds to the request sent by microprocessor 340 and transmits the requested data to serial input/output interface 360. Interface 360 then passes the requested data to microprocessor 340.

In addition to storing data similar to that stored in memory 28A, memory 28C also stores information regarding motor assembly 260. For example, in a preferred embodiment, memory 28C stores a model type and speed/torque data for the motor in motor assembly 260. Other characteristics regarding the motor in motor assembly 260 may also be stored in memory 28C. The model type, speed/torque data and/or other stored motor characteristics are used by microprocessor 340 to determine the appropriate control signals to send to motor drive 380. It is desirable for the motor assembly 260 to linearly increase the force applied to a patient. However, DC motors typically tend to slow down as a load is applied. The voltage may have to be increased as the load increases in order to obtain a linear increase in force. Microprocessor 340 can make use of the motor information obtained from memory 28C, and make appropriate adjustments in the signals sent to motor drive 380 to overcome the natural tendency of the motor to slow down as a load is applied.

A time stamp of the last test of sensor interface assembly 226 is stored in memory 28B, and a time stamp of the last test of motor assembly 260 is stored in memory 28C. Sensor interface assembly 226 and motor assembly 260 are tested by selecting appropriate inputs 450a–450h on display device 280. The test results are displayed on one or more of displays 460a–460c and 480. Sensor interface assembly 226 and motor assembly 260 are preferably tested at least once every 24 hours. An indication is displayed on control and display device 280 when sensor interface assembly 226 and motor assembly 260 need testing. Motor assembly 260 and sensor interface assembly 226 are detachable from each other as well as from control and display device 280, and may be replaced by other motor assemblies and sensors. Control and display device 280 preferably uses the older of the motor assembly 260 test time and the sensor interface assembly 226 test time (i.e., worst case) in determining if testing should be performed. The use of a time stamp facilitates portability of measurement device 220. The measurement device 220 may be placed on a patient in one room (pre-op for example), disconnected from the control and display device 280 in that room, and reconnected to another control and display device 280 installed permanently in another room (e.g., an operating room). The time stamp information allows the second control and display device 280 to know whether the measurement device 220 was tested recently, or whether it needs testing.

Although the present invention has been described with reference to preferred embodiments, workers skilled in the art will recognize that changes may be made in form and detail without departing from the spirit and scope of the invention. As just one example, the blood pressure measuring device embodiments disclosed herein are just a few of the many different embodiments that can make use of a memory or memories for storing data such as sensor characteristics and history information, and use the stored data for purposes such as calibration, generation of status indications, automatic identification of appropriate algorithms for control and data manipulation, service and billing. Such memory usage may be implemented with any of the device embodiments disclosed in the above-mentioned Medwave patents and patent applications, which are incorporated by reference.

What is claimed is:

1. A non-invasive blood pressure measurement device for determining blood pressure of an artery, the device comprising:

a sensor which is adapted to be pressed against the artery to produce blood pressure signals;

a non-volatile memory carried by the sensor for storing data including sensor history information, the sensor history information including a stamp of a last test of the sensor;

means for determining whether the sensor should be tested based on the stamp of the last test of the sensor;

means for providing an indication that new testing should be performed;

means for performing a test of the sensor; and means for displaying results of the test of the sensor.

2. The device of claim 1, wherein the stamp of a last test of the sensor includes a time and a date.

3. The device of claim 1, wherein the non-volatile memory also stores a sensor date code, and wherein the device updates sensor expiration data based on the sensor date code and displays the updated sensor expiration data.

4. A non-invasive blood pressure measurement device for determining blood pressure of an artery, the device comprising:

a sensor which is adapted to be pressed against the artery to produce blood pressure signals; and a non-volatile memory carried by the sensor for storing data including sensor history information including a stamp of a last test of the sensor;

wherein the device identifies and uses appropriate device control algorithms based upon data retrieved from the non-volatile memory.

5. A non-invasive blood pressure measurement device for determining blood pressure of an artery, the device comprising:

a sensor which is adapted to be pressed against the artery to produce blood pressure signals; and a non-volatile memory carried by the sensor for storing data including sensor history information involving a stamp of a last test of the sensor;

wherein the device identifies and uses appropriate data manipulation algorithms based upon data retrieved from the non-volatile memory.

6. A non-invasive blood pressure measurement device for determining blood pressure of an artery, the device comprising:

a sensor which is adapted to be pressed against the artery to produce blood pressure signals; and a non-volatile memory carried by the sensor for storing data including sensor history information including a stamp of a last test of the sensor;

wherein the non-volatile memory also stores a checksum that is based on data stored in the non-volatile memory.

7. A non-invasive blood pressure measurement system for determining blood pressure of an artery, the system comprising:

a sensor which is adapted to be pressed against the artery to produce blood pressure signals;

a first non-volatile memory carried by the sensor for storing data including sensor history information;

an instrument connected to the sensor and the first non-volatile memory for providing blood pressure values based upon the blood pressure signals;

a wrist module attachable to a patient's wrist and including a drive assembly connectable to the sensor for applying force to cause the sensor to be pressed against the patient's wrist, the wrist module connected to the instrument, the drive assembly controlled by the instrument; and a second non-volatile memory carried by the drive assembly for storing drive assembly information, the drive assembly information including data characterizing the drive assembly.

8. The system of claim 4, wherein the drive assembly information includes a time stamp of a last test of the drive assembly.

9. The system of claim 8, wherein the time stamp includes a time and a date.

10. The system of claim 4, wherein the sensor history information includes a time stamp of a last test of the sensor.

11. The system of claim 10, wherein the time stamp includes a time and a date.

12. The system of claim 4, wherein the instrument reads and updates the sensor history information and drive assembly information.

13. The system of claim 4, wherein the instrument reads data from the first and the second non-volatile memories to determine when the sensor and the drive assembly were last tested.

14. The system of claim 13, wherein the instrument provides a notification when the sensor and the drive assembly should be tested.

15. The system of claim 4, wherein the first non-volatile memory also stores a sensor date code, and wherein the instrument updates sensor expiration data based on the sensor date code and displays the updated sensor expiration data.

16. The system of claim 15, wherein the sensor date code represents a sensor initialization date from which a sensor expiration date is determined.

17. The system of claim 4, wherein the first non-volatile memory also stores model type data, and wherein the system identifies and uses appropriate control algorithms based upon data retrieved from the first non-volatile memory.

18. The system of claim 4, wherein the first non-volatile memory also stores model type data, and wherein the system identifies and uses appropriate data manipulation algorithms based upon data retrieved from the first non-volatile memory.

19. The system of claim 4, wherein the first and the second non-volatile memories also store a checksum based on data stored in the non-volatile memories.

* * * * *

UNITED STATES PATENT AND TRADEMARK OFFICE
CERTIFICATE OF CORRECTION

PATENT NO. : 6,241,679 B1　　　　　　　　　　　　　　　　　　　　　　Page 1 of 1
DATED : June 5, 2001
INVENTOR(S) : Timothy G. Curran It is certified that error appears in the above-identified patent and that said Letters Patent is hereby corrected as shown below:

Column 2,
Line 24, delete "ia", insert -- is --

Column 5,
Line 13, delete "arc", insert -- are --

Column 15,
Line 33, delete "4", insert -- 7--

Column 16,
Lines 1, 5, 8, 15, 23, 27 and 32, delete "4", insert -- 7 --

Signed and Sealed this

Eleventh Day of June, 2002

*Attest:*

*Attesting Officer*

JAMES E. ROGAN
*Director of the United States Patent and Trademark Office*